United States Patent [19]

Dunbar et al.

[11] 4,058,520

[45] Nov. 15, 1977

[54] AMINOALKYLTHIOPYRIDAZINE COMPOUNDS

[75] Inventors: Joseph E. Dunbar; Louis E. Begin, both of Midland, Mich.

[73] Assignee: The Dow Chemical Company, Midland, Mich.

[21] Appl. No.: 684,224

[22] Filed: May 7, 1976

[51] Int. Cl.² ............................................. C07D 237/18
[52] U.S. Cl. ........................... 260/239 B; 260/250 A; 260/243.3; 544/114; 544/82; 424/248.52; 424/250
[58] Field of Search .................. 260/250 A, 239 B

[56] References Cited

U.S. PATENT DOCUMENTS

| | | | |
|---|---|---|---|
| 3,950,353 | 4/1976 | Durant et al. | 260/250 A |
| 3,979,398 | 9/1976 | White | 260/250 A |
| 3,980,633 | 9/1976 | Kropp et al. | 260/250 A |

*Primary Examiner*—Donald G. Daus
*Assistant Examiner*—David E. Wheeler
*Attorney, Agent, or Firm*—James W. Ambrosius

[57] ABSTRACT

This invention concerns novel aminoalkylthiopyridazine compounds useful for inhibiting the aggregation of blood platelets in animals and a process for preparing the compounds from an isothiuronium salt generated in situ from an aminoalkyl halide and thiourea. The compounds also have fungicidal and nematocidal properties.

7 Claims, No Drawings

AMINOALKYLTHIOPYRIDAZINE COMPOUNDS

BACKGROUND OF THE INVENTION

Adenosine diphosphate, hereafter called ADP, is a principle factor in the aggregation of blood platelets. Platelet aggregation in the blood stream of a mammal can lead to the formation of a thrombos. Agents which interfere with ADP induced platelet aggregation are of use as antithrombotic drugs.

The preparation of 3-dialkylaminopyridazines and their use as neuromuscular blocking agents was described by Steck and Fletcher in *J. Hetercyclic Chem.* 11, p. 1077, (1974).

SUMMARY OF THE INVENTION

The compounds that are the subject of the present invention are represented by the general formula:

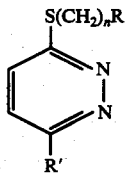

wherein R is loweralkylamino, diloweralkylamino, or a simple heterocyclic amino radical selected from the group of piperidinyl, morpholinyl, and hexamethyleneimino;

R' is a halogen or an alkylthioamino group having the formula:

where $n$ is an integer of from 1 to 5 and R is as defined hereinbefore. As used herein, the term loweralkyl refers to an alkyl having from 1 to 4 carbon atoms.

It is therefore understood that the compounds that are the subject of this invention are pyridazines having ring substitutions in the 3 and 6 positions. It is further seen that said substitution may be 3,6-bis-(aminoalkylthio) in which case both substitutions are identical or alternatively 3-halo-6-(aminoalkylthio) in which case the substitutions are different. These compounds are useful in inhibiting the aggregation of blood platelets in animals. They also are useful in certain agricultural applications as fungicides and nematocides.

The invention also includes the pharmaceutically acceptable salts of the aminoalkylthiopyridazine compounds described herein. As used in the specification and claims, the term "pharmaceutically acceptable salts" refers to non-toxic acid addition salts of the aminoalkylthiopyridazine compounds, the anions of which are relatively innocuous to animals at dosages consistent with good platelet aggregation inhibition so that the beneficial effects of the free base are not vitiated by side effects ascribable to the anions. Pharmaceutically acceptable salts include those derived from mineral acids such as hydrochloric, hydrobromic, sulfuric, and nitric acids and from organic acids such as acetic, lactic, maleic, succinic, fumaric, glutaric, citric, malic, p-toluenesulfonic, methanesulfonic and tartaric acids, and the like.

One process suitable for preparing the compounds is by generating a corresponding aminoalkylthio intermediate either from a corresponding isolated isothiuronium salt or from said salt which is generated in situ from the corresponding aminoalkyl halide, usually a chloride, and thiourea. In the latter case, the products can be obtained in a "one pot" synthesis from the aminoalkyl halide or salt thereof, thiourea, sodium hydroxide, and 3,6-dihalopyridazine. The reaction is carried out in a two phase organic system, using a quaternary salt as a phase transfer catalyst.

In preparing the 3-halo-6-(aminoalkylthio) substituted pyridazines, good yields are obtained when the reactants are mixed in the proportions of 1 mole of aminoalkyl halide, 1 mole thiourea, and 2 to 3 moles of sodium hydroxide. After the reaction of the above mixture, 1 mole 3,6-dihalopyridazine is added.

DETAILED DESCRIPTION OF THE INVENTION

It has been found that the aminoalkylthiopyridazine compounds used in accordance with the invention, when administered to animals and in particular to mammals, has the effect of inhibiting the ADP induced aggregation of blood platelets. The compounds can be administered orally or parenterally by subcutaneous, intravenous or intraperitoneal injection or by implantation or the like, oral administration being preferred. The aminoalkylthiopyridazines are preferably administered as pharmaceutical compositions in dosage unit forms.

In forming compositions of the invention, the active ingredient is incorporated in a pharmaceutical carrier. The term "pharmaceutical carrier" refers to pharmaceutical excipients and includes nutritive compositions such as a solid or liquid foodstuff. In the present specification and claims, "pharmaceutical excipient" refers to known pharmaceutical excipients which are substantially non-toxic and non-sensitizing at dosages consistent with good platelet aggregation inhibiting activity. A preferred pharmaceutical carrier is a surface active dispersing agent.

Suitable solid pharmaceutical carriers which can be employed for formulating the compositions of the invention include starch, lactose, glucose, sucrose, gelatin, microcrystalline cellulose, powdered licorice, powdered tragacanth, malt, rice flour, silica gel, magnesium stearate, magnesium carbonate, hydroxypropyl methyl cellulose, chalk and the like, and compatible mixtures thereof. In the preparation of solid compositions, the active ingredient can be triturated with a solid pharmaceutical carrier or mixtures thereof, or otherwise mechanically milled to obtain a uniform mixture. The mixtures can be compressed into tablets or filled into capsules by known procedures, or they can be employed as powders or the like. The solid compositions generally contain from about 0.02 to about 90, inclusive, percent by weight of the active ingredient.

Among the liquid pharmaceutical carriers which can be utilized are ethyl alcohol, propylene glycol, polyethylene glycols, peanut oil, corn oil, water, saline solution, glycerine and water mixtures, glucose syrup, syrup of acacia, mucilage of tragacanth and the like, and compatible methods thereof.

The compositions can also contain the active ingredient in admixture with surface-active dispersing agents and, optionally, an inert carrier. Suitable surface-active dispersing agents include natural phosphatides such as lecithin, natural gums such as gum acacia oxide with fatty acids, such as polyoxyethylene stearate, condensation products of ethylene oxide with fatty alcohols such as heptadecaethyleneoxycetanol and esters or partial esters of fatty acids with a hexitol or hexitol anhydride, and their condensation products with ethylene oxide, such as sorbitan monooleate, polyoxyethylene sorbitan monooleate and polyoxyethylene sorbitan monooleate. Such compositions can be in the form of emulsions, suspensions or dispersible powders or granules, and the compositions containing surface-active dispersing agents can also be in the form of tablets, capsules, or the like.

The pharmaceutical compositions described above can also contain, in addition, sweetening agents such as sugar, saccharin or the like, flavoring agents such as carmel, preservatives such as ethyl p-hydroxybenzoate, antioxidants such as ascorbic acid and suitable coloring materials.

The aminoalkylthiopyridazine compounds can also be incorporated in a foodstuff such as, for example, butter, margarine, edible oils and the like. The active compounds can also be prepared in the form of a nutritive composition in which the active ingredient is mixed with vitamins, fats, proteins or carbohydrates and the like, or mixtures thereof. Such compositions can be prepared in liquid form such as emulsions or suspensions, as well as in solid form. The nutritive compositions are adapted to be administered as the total diet. The nutritive compositions preferably contain from 0.02 to about 2 percent of the active ingredient when administered as the total diet. The compositions can contain higher concentrations of the active ingredient when administered as a supplement.

The aminoalkylthiopyridazines can also be formulated as concentrated compositions which are adapted to be diluted by admixture with liquid or solid foodstuffs. The concentrated compositions are prepared by mechanically milling or otherwise mixing the active ingredient with an inert carrier such as silica gel, soluble casein, starch or the like, or mixtures thereof. The concentrated compositions can also include additional ingredients such as vitamins, preservatives, antioxidants and flavoring agents. Such compositions contain from 5 to about 90 percent of active ingredient.

The following examples illustrate the present invention but are not to be construed as a limitation thereon.

EXAMPLE 1

Preparation of
3-Chloro-6-(2-(1-piperidinyl)ethylthio)pyridazine

To a warm, stirred solution of 11.4 g (0.150 mole) of thiourea in 175 ml of ethanol was added 22.1 g (0.150 mole) of 1-(2-chloroethyl)piperidine. The resulting solution was heated under reflux for 4 hours. The ethanol was then removed by evaporation in vacuo, and the semisolid residue was taken up in a solution of 12.0 g (0.300 mole) of sodium hydroxide in 180 ml of water. The solution, thus prepared, was added with vigorous stirring to a solution of 22.2 g (0.149 mole) of 3,6-dichloropyridazine and 0.53 g of benzyltriethylammonium chloride in 500 ml of toluene. The mixture was heated under reflux with vigorous stirring for 2 hours, after which period of time the mixture was cooled to room temperature, and the toluene phase was separated. The aqueous phase was extracted with one portion of toluene, and the extract was added to the said toluene phase. The toluene solution, thus obtained, was dried over anhydrous sodium sulfate, filtered and the toluene was removed from the filtrate by evaporation in vacuo. The solid residue was recrystallized from propanol-2 to give 27.3 (71%) of the 3-chloro-6-(2-(1-piperidinyl)ethylthio)pyridazine as white, fibrous crystals. The product was found to melt at 103.5 to 104° C and to have carbon, hydrogen, and nitrogen contents of 51.3%, 6.21%, and 16.36%, respectively, as compared to theoretical contents of 51.25%, 6.26%, and 16.30%.

EXAMPLE 2

3-Chloro-6-(2-(hexamethyleneimino)ethylthio)pyridazine

To a solution of 11.9 g (0.0802 mole) of 3,6-dichloropyridazine and 0.3 g of benzyltriethylammonium chloride in 270 ml of toluene was added a solution of 22.0 g (0.0802 mole) of 2-(hexamethyleneimino)ethylisothiourea dihydrochloride in 50 ml of water followed by the addition of a solution of 9.6 g (0.24 mole) of sodium hydroxide in 50 ml of water. The reaction mixture was heated under reflux with vigorous stirring for a period of 3 hours and then cooled to room temperature. The separated toluene phase was washed with a saturated sodium chloride solution, and the aqueous phase was extracted with two portions of toluene, which were then combined with said toluene phase. The toluene solution, thus obtained, was dried over anhydrous sodium sulfate, filtered, and evaporated to dryness, leaving an amber oil, which crystallized upon cooling. Recrystallization of the crude substance from methylcyclohexane yielded 13.1 of cream colored crystals of 3-chloro-6-(2-(hexamethyleneimino)ethylthio)pyridazine. A second recrystallization gave a product with a melting point of 74.5°–76.5° C.

Elemental analysis showed carbon 53.3%, hydrogen 6.77%, and nitrogen 15.36% as compared to theoretical values of 52.02% carbon, 6.67% hydrogen, and 15.46% nitrogen.

EXAMPLE 3

3-Chloro-6-(3-(diethylamino)propylthio)pyridazine

A solution of 22.5 g (0.150 mole) of N-(3-chloropropyl)-N,N-diethylamine and 11.4 g (0.150 mole) of thiourea in 175 ml of ethanol was heated under reflux with stirring for 3.5 hours. The ethanol was then removed by evaporation in vacuo, leaving a semisolid residue which was taken up in a solution, consisting of 12.0 g (0.300 mole) of sodium hydroxide in 180 ml of water. The resulting mixture was added to a solution of 22.3 g (0.150 mole) of 3,6-dichloropyridazine and 0.6 g of benzyltriethylammonium chloride in 500 ml of toluene. The reaction mixture was heated under reflux with vigorous stirring for 2 hours and then cooled to room temperature. The toluene layer was separated from the aqueous layer, and the latter was extracted with three portions of toluene. The extract was combined with the toluene phase and the solution dried over anhydrous sodium sulfate. After the sodium sulfate had been removed by filtration, the toluene was removed by evaporation in vacuo, leaving a yellow oil, which was purified by column chromatography on silica gel. Unreacted, 3,6-dichloropyridazine (7.1 g, mp 67°–69° C) was isolated by elution with ethyl acetate. Elution with pyridine provided 16.6 g of the product as a brown oil after removal of the pyridine by distillation at reduced pressure. On standing 7 days, the oil partially crystallized. The tan crystals were removed by filtration; and, after drying in vacuo over concentrated sulfuric acid the 3-chloro-6-(3-(diethylamino)propylthio)pyridazine was found to melt at 27° C.

Elemental analysis showed carbon 51.0%, hydrogen 6.97%, and nitrogen 16.23% as compared to calculated values of 50.85% carbon, 6.98% hydrogen, and 16.17% nitrogen.

EXAMPLE 4

3-Chloro-6-(3-(4-morpholinyl)propylthio)pyridazine

A solution of 24.5 g (0.150 mole) of 4-(3-chloropropyl)morpholine and 11.4 g (0.150 mole) of thiourea in 175 ml of ethanol was heated under reflux for 3 hours. The ethanol was removed by distillation in vacuo, and the residual syrup was dissolved in a solution of 12.0 g (0.300 mole) of sodium hydroxide in 180 ml of water. The solution, thus obtained, was added to a solution of 22.3 g (0.150 mole) of 3,6-dichloropyridazine and 0.53 g of benzyltriethylammonium chloride in 500 ml of toluene. The mixture was then heated under reflux with vigorous stirring for 2.5 hours and allowed to cool to room temperature. The toluene layer was separated, and the aqueous layer was washed with toluene, the washings being combined with the original toluene portion. This solution was dried over anhydrous potassium carbonate, filtered and concentrated, causing the crystallization of 25.5 g of the 3-chloro-6-(3-(4-morpholinyl)propylthio)pyridazine as a white solid having a melting point of 105.5°–106° C.

Elemental analysis showed carbon 48.3%, hydrogen 5.90%, and nitrogen 15.31% as compared to calculated values of 48.28% carbon, 5.89% hydrogen, and 15.35% nitrogen.

EXAMPLE 5

3,6-Bis(2-(4-morpholinyl)ethylthio)pyridazine

A mixture was prepared containing 14.0 grams (0.0951 mole) of 2-(morpholino)ethanethiol, 50 ml of dimethyl sulfoxide, 50 ml of water and 19.0 grams (0.0950 mole) of 20% aqueous sodium hydroxide. The mixture was stirred and warmed to 50° C. A quantity (7.1 grams, 0.048 mole) of 3,6-dichloropyridazine was added to the mixture. The temperature of the reaction mass rose to 105° C and external cooling was required. The mixture was diluted with water, and the precipitate was collected on a filter. The crude 3,6-bis(2-(4-morpholinyl)ethylthio)pyridazine was recrystallized wet from ethanol to give a white crystalline solid having a melting point of 102.5°–103.5° C.

Elemental analysis showed carbon 51.91%, hydrogen 6.99% and nitrogen 15.22% as compared to theoretical percentages of carbon 51.86%, hydrogen 7.07%, and nitrogen 15.12%.

The process wherein an isothiourea salt is converted under aqueous alkaline conditions to the corresponding thiol in situ is also exemplified in Examples 1–4 above. In Example 2, the previously prepared and isolated isothiourea dihydrochloride was used to prepare the product. In Examples 1, 3 and 4, the isothiourea monohydrochlorides, which convert spontaneously to the corresponding thiols under basic conditions, were prepared but not isolated or purified since the resulting thiol degradation product was desired.

Solvents used in the preparation of the isothiourea monohydrochlorides are preferably inert polar solvents such as, for example, ethanol, isopropyl alcohol, dimethylformamide, dimethylsulfoxide, and butanol. Solvents used in the reaction of the in situ thiols with the 3,6-dichloropyridazines must be inert, water immiscible solvents such as, for example, benzene, toluene, xylene, or chloroform.

Other aminoalkylthiopyridazine compounds prepared using the general procedure described above were the following.

3-Chloro-6-(2-(4-morpholinyl)ethylthio)pyridazine, melting point 100°–101° C.

6-Chloro-3-(2-(diisopropylamino)ethylthio)pyridazine, melting point 57.5°–59° C.

3-Chloro-6-(3-dimethylamino)propylthio)pyridazinium methane sulfonate, melting point 174°–175° C.

EXAMPLE 6

Emboli formed in the vascular system of mice in response to the administration of ADP cause a stroke-like response that prevents mice from staying on an inclined screen. To illustrate the platelet aggregation inhibition effect of the aminoalkylthiopyridazines, ten mice were dosed orally with 60 mgs per kilogram of body weight of the compound 6-chloro-3-(2-diisopropylamino)ethylthio)pyridazine. One hour after compound administration, the mice were challenged with ADP (0.05 M mole/kg) by injection via the tail vein and placed on an inclined screen. The unprotected control mice were unable to maintain their position on the screen.

All 10 of the mice treated with 6-chloro-3-(2-diisopropylamino)ethylthio)pyridazine were found to be protected from the ADP challenge and remained on the screen.

EXAMPLE 7

The effect of the pyridazine compounds were demonstrated by conventional techniques originally described by Born in Nature, 194, 927 (1962). Platelet aggregation was initiated in vitro by 0.125 to 0.25 mg/ml of ADP. Rat blood was collected into 3.0% trisodium citrate solution (1:10) by cardiac puncture under methoxyfurane anesthesia. The blood was centrifuged at 120 g for 10 minutes at room temperature and the supernatant platelet rich plasma was removed and diluted with lactated Ringer's solution containing the pyridazine aggregation inhibiting agent (1.0:1.5). Samples of 1.0 ml were pipetted into plastic test tubes and incubated for 10 minutes. Plastic equipment was used for all procedures. The concentration of the pyridazine compound in micromoles inhibiting ADP aggregation by 50% ($IC_{50}$) was determined using changes in optical density as an indicium of platelet aggregation. The results are shown in Table I.

TABLE I

| Compound Name | $IC_{50}$ADP* |
|---|---|
| 3-chloro-6-(2-(4-morpholinyl)ethylthio)-pyridazine | 2.6 μM/ml |
| 3,6-Bis(2-(4-morpholinyl)ethylthio)-pyridazine | 13.78 μM/ml |
| 6-chloro-3-(2-(diisopropylamino)ethylthio)-pyridazine | 0.14 μM/ml |
| 3-chloro-6-(3-(dimethylamino)propylthio)-pyridazinium methanesulfonate | 2.4 μM/ml |
| 3-chloro-6-(2-(1-piperidinyl)ethylthio)-pyridazine | 3.3 μM/ml |
| 3-chloro-6-(2-(hexamethyleneimino)ethylthio)-pyridazine | 2.43 μM/ml |
| 3-chloro-6-(3-(diethylamino)propylthio)-pyridazine | 3.71 μM/ml |
| 3-chloro-6-(3-(4-morpholinyl)propylthio)-pyridazine | 10.47 μM/ml |

*Concentration in micromoles at which ADP induced platelet aggregation is inhibited by 50%.

The data indicate that the compound 6-chloro-3-(2-(diisopropylamino)ethylthio)pyridazine is highly effective as a platelet aggregation inhibitor. Other compounds tested while less active also showed satisfactory activity.

In addition to the platelet aggregation inhibiting activity described above, the compound 3,6-bis-(2-(4-morpholinyl)ethylthio)pyridazine has been shown to be 100% effective in the control and killing of the fungus *Verticillium albo* at a concentration of 100 parts per million. The same compound has also been shown to be 90% effective against apple scab when used at a concentration of 400 parts per million. The compound 3-chloro-6-(3-(diethylamino)propylthio)pyridazine has been shown to be 100% effective as a fungicide in the killing and control of tobacco black root rot at a concentration of only 25 parts per million.

The compound 3-chloro-6-(2-(4-morpholinyl)ethylthio)pyridazine has also been shown to be 90% effective in the killing and control of rootknot nematode when applied at a concentration of 2.4 pounds per 100 cu. ft. of soil.

I claim:

1. A compound corresponding to the formula

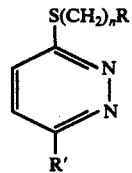

and the pharmaceutically acceptable salts thereof wherein R is loweralkylamino, diloweralkylamino or a simple heterocyclic amino radical selected from the group consisting of piperidinyl, and hexamethyleneimino;

R' is a halogen or an alkylaminoalkylthio group having the formula

—S(CH$_2$)$_n$R;

where $n$ is an integer of from 1 to 5 and R is as defined hereinbefore.

2. The compound of claim 1 wherein R' is chloro.
3. The compound of claim 2 which is 6-chloro-3-(2-diisopropylamino)ethylthio)pyridazine.
4. The compound of claim 2 which is 3-chloro-6-(3-(dimethylamino)propylthio)pyridazine.
5. The compound of claim 2 which is 3-chloro-6-(2-(1-piperidinyl)ethylthio)pyridazine.
6. The compound of claim 2 which is 3-chloro-6-(2-(hexamethyleneimino)ethylthio)pyridazine.
7. The compound of claim 2 which is 3-chloro-6-(3-(diethylamino)propylthio)pyridazine.

* * * * *